US006982165B2

(12) United States Patent
Yamakawa et al.

(10) Patent No.: US 6,982,165 B2
(45) Date of Patent: Jan. 3, 2006

(54) NUCLEIC ACID SEQUENCING BY RAMAN MONITORING OF MOLECULAR DECONSTRUCTION

(75) Inventors: Mineo Yamakawa, Campbell, CA (US); Andrew Berlin, San Jose, CA (US); Steve Kirch, Pleasanton, CA (US); Gabi Neubauer, Los Gatos, CA (US); Valluri Rao, Saratoga, CA (US)

(73) Assignee: Intel Corporation, Santa Clara, CA (US)

( * ) Notice: Subject to any disclaimer, the term of this patent is extended or adjusted under 35 U.S.C. 154(b) by 41 days.

(21) Appl. No.: 09/962,555

(22) Filed: Sep. 24, 2001

(65) Prior Publication Data

US 2003/0058799 A1    Mar. 27, 2003

(51) Int. Cl.
C12M 1/34    (2006.01)
C12Q 1/68    (2006.01)
(52) U.S. Cl. .................... 435/287.2; 435/6; 435/288.7; 204/182.8
(58) Field of Classification Search ................ 435/6, 435/287.2, 288.7; 204/182.8
See application file for complete search history.

(56) References Cited

U.S. PATENT DOCUMENTS

| 4,962,037 | A |   | 10/1990 | Jett et al. |         |
|-----------|---|---|---------|-------------|---------|
| 5,306,403 | A | * | 4/1994  | Vo-Dinh et al. | 204/182.8 |
| 5,405,747 | A |   | 4/1995  | Jett et al. |         |
| 5,674,743 | A | * | 10/1997 | Ulmer       | 435/287.2 |
| 5,707,804 | A |   | 1/1998  | Mathies et al. |       |
| 5,721,102 | A |   | 2/1998  | Vo-Dinh     |         |
| 5,776,674 | A |   | 7/1998  | Ulmer       |         |
| 5,783,389 | A |   | 7/1998  | Vo-Dinh     |         |
| 5,814,454 | A |   | 9/1998  | Ju          |         |
| 5,814,516 | A |   | 9/1998  | Vo-Dinh     |         |
| 5,866,336 | A |   | 2/1999  | Nazarenko et al. |    |
| 6,002,471 | A |   | 12/1999 | Quake       |         |
| 6,127,120 | A |   | 10/2000 | Graham et al. |       |
| 6,136,543 | A |   | 10/2000 | Anazawa et al. |      |
| 6,140,053 | A |   | 10/2000 | Koster      |         |
| 6,174,677 | B1| * | 1/2001  | Vo-Dinh     | 435/6   |
| 6,214,246 | B1|   | 4/2001  | Craighead   |         |
| 6,225,068 | B1|   | 5/2001  | Wolfrum     |         |

FOREIGN PATENT DOCUMENTS

| WO | WO 99/44045 | * | 9/1999  |
|----|-------------|---|---------|
| WO | WO 00/70073 |   | 11/2000 |

OTHER PUBLICATIONS

Ambrose, W. Patrick et al., "Application of Single Molecule Detection to DNA Sequencing and Sizing", *Ber. Bunseges. Phys. Chem.*, 97(12):1535-1542.
Castro, A. et al., "Fluorescence Detection and Size Measurement of Single DNA Molecules," *Analytical Chemistry,* *American Chemical Society*, 65(7):849-852, Elsevier (1993).
Dorre, Klaus et al., "Techniques for single molecule sequencing", *Bioimaging.*, 5(3):139-152 (1997).
Goodwin, Peter M. et al., "Single-Molecule Detection in Liquids by Laser-Induced Fluorescence", *Acc. Chem. Res.*, 29:607-613 (1996).
Goodwin, Peter M. et al., "Application of Single Molecule Detection to DNA Sequencing," *Nucleosides and Nucleotides*, 16(5/6)543-550 (1997).
Goodwin, Peter M. et al., "Progress toward DNA sequencing at the single molecule level," *Experimental technique of Physics*, 41(2):279-294, (1995).
Schecker, Jay A. et al., "Flow-Based Continuous DNA Sequencing Via Single Molecule Detection of Enzymatically Cleaved Fluorescent Nucleotides," *SPIE*, 2386:4-12 (1995).
Szoelloesi, J. et al., "Application of Fluorescence Resonance Energy Transfer in the Clinical Laboratory: Routine and Research," *Cytometry*, 34(4):159-179 (1998).
Uibel, Rory H. and Harris, Joel M. "Fiber-Optic Raman Spectroscopy for *in Situ* Monitoring of Metal-Ion Complexation by Ligands Immobilized onto Silica Gel," *Applied Spectroscopy*, 54(12):1868-1875 (2000).
Watson, N. et al., "Detection of a DNA Sequence by Surface Enhanced Resonance Raman Scattering of a Modified DNA Probe," *Progress in Forensic Genetics*, 7(1167):6-8 (1998).
Weiss, Shimon, "Fluorescence Spectyroscopy of Single Biomolecules" *Science*, 283(5408):1676-1683 (1999).
Machara, N. et al., Efficient Detection of Single Molecules Eluting Off an Optically Trapped Microsphere, *Bioimaging* 6 (1998), 33-42, 1998.
1997 DOE Human Genome Program Contractor-Grantee Workshop VI, pp. 23-25, Retrieved from the Internet URL: <http://www.ornl.gov/hgmis/publicat/97santa/seqtech.html.
M. Sauer, New Strategies for DNA Sequencing Using Diode Laser-Based Time-Resolved Fluorescence Detection [Retrieved on Nov. 12, 2001]. Retrieved from the Internet URL: <http://pc-cube01.pci.uni-heidelberg.de/alt/msauer/emsproject01.htm. 2 pages.

* cited by examiner

Primary Examiner—Jeffrey Fredman
(74) Attorney, Agent, or Firm—DLA Piper Rudnick Gray Cary US LLP

(57) ABSTRACT

The disclosed methods, apparatus and compositions are of use for nucleic acid sequencing. More particularly, the methods and apparatus concern sequencing single molecules of single stranded DNA or RNA by exposing the molecule to exonuclease activity, removing free nucleotides one at a time from one end of the nucleic acid, and identifying the released nucleotides by Raman spectroscopy or FRET.

16 Claims, 2 Drawing Sheets

NUCLEIC ACID SEQUENCING BY RAMAN MONITORING OF MOLECULAR DECONSTRUCTION

FIELD OF THE INVENTION

The present methods, compositions and apparatus relate to the fields of molecular biology and genomics. More particularly, the methods, compositions and apparatus concern nucleic acid sequencing.

BACKGROUND

The advent of the human genome project required that improved methods for sequencing nucleic acids, such as DNA (deoxyribonucleic acid) and RNA (ribonucleic acid), be developed. Genetic information is stored in the form of very long molecules of DNA organized into chromosomes. The twenty-three pairs of chromosomes in the human genome contain approximately three billion bases of DNA sequence. This DNA sequence information determines multiple characteristics of each individual, such as height, eye color and ethnicity. Many common diseases, such as cancer, cystic fibrosis, sickle cell anemia and muscular dystrophy are based at least in part on variations in DNA sequence.

Determination of the entire sequence of the human genome has provided a foundation for identifying the genetic basis of such diseases. However, a great deal of work remains to be done to identify the genetic variations associated with each disease. That would require DNA sequencing of portions of chromosomes in individuals or families exhibiting each such disease, in order to identify specific changes in DNA sequence that promote the disease. RNA, an intermediary molecule required for processing of genetic information, can also be sequenced in some cases to identify the genetic bases of various diseases.

Existing methods for nucleic acid sequencing, based on detection of fluorescently labeled nucleic acids that have been separated by size, are limited by the length of the nucleic acid that can be sequenced. Typically, only 500 to 1,000 bases of nucleic acid sequence can be determined at one time. This is much shorter than the length of the functional unit of DNA, referred to as a gene, which can be tens or even hundreds of thousands of bases in length. Using current methods, determination of a complete gene sequence requires that many copies of the gene be produced, cut into overlapping fragments and sequenced, after which the overlapping DNA sequences may be assembled into the complete gene. This process is laborious, expensive, inefficient and time-consuming.

BRIEF DESCRIPTION OF THE DRAWINGS

The following drawings form part of the present specification and are included to further demonstrate certain aspects of the disclosed embodiments. The embodiments may be better understood by reference to one or more of these drawings in combination with the detailed description of specific embodiments presented herein.

DESCRIPTION OF ILLUSTRATIVE EMBODIMENTS

The disclosed methods, compositions and apparatus are of use for the rapid, automated sequencing of nucleic acids. In particular embodiments, the methods, compositions and apparatus are suitable for obtaining the sequences of very long nucleic acid molecules of greater than 1,000, greater than 2,000, greater than 5,000, greater than 10,000 greater than 20,000, greater than 50,000, greater than 100,000 or even more bases in length. In various embodiments, such sequence information may be obtained during the course of a single sequencing run, using one molecule of nucleic acid 13, 102. In other embodiments, multiple copies of the nucleic acid molecule 13, 102 may be sequenced in parallel or sequentially to confirm the nucleic acid sequence or to obtain complete sequence data. In alternative embodiments, both the nucleic acid molecule 13, 102 and its complementary strand may be sequenced to confirm the accuracy of the sequence information. Advantages over prior methods of nucleic acid sequencing include the ability to read long nucleic acid sequences in a single sequencing run, greater speed of obtaining sequence data, decreased cost of sequencing and greater efficiency in terms of the amount of operator time required per unit of sequence data generated.

In certain embodiments, the nucleic acid 13, 102 to be sequenced is DNA, although it is contemplated that other nucleic acids 13, 102 comprising RNA or synthetic nucleotide analogs could be sequenced as well. The following detailed description contains numerous specific details in order to provide a more thorough understanding of the disclosed embodiments. However, it will be apparent to those skilled in the art that the embodiments may be practiced without these specific details. In other instances, devices, methods, procedures, and individual components that are well known in the art have not been described in detail herein.

Figure 1:
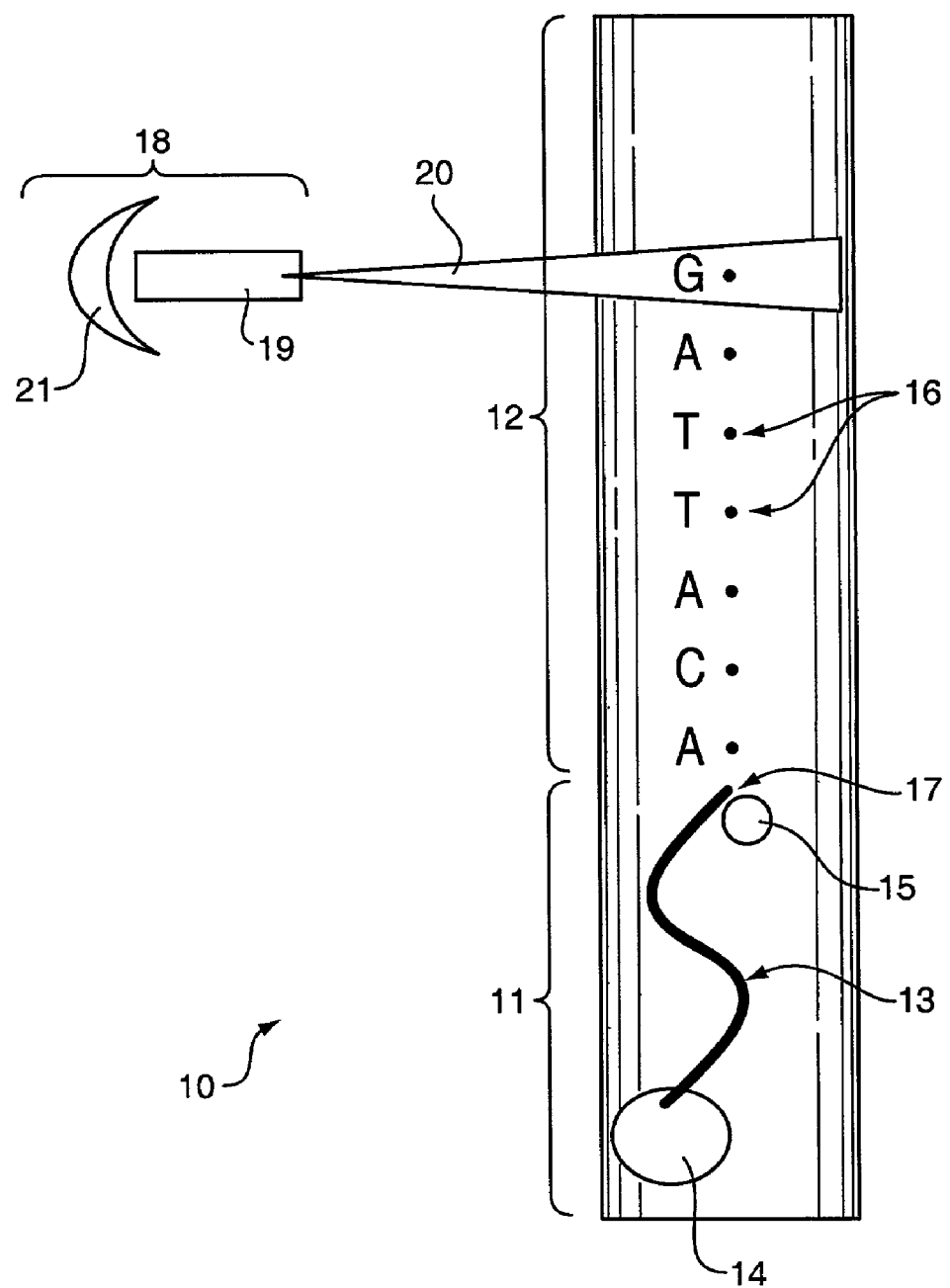
FIG. 1 illustrates an exemplary apparatus (not to scale) and method for DNA sequencing in which the released nucleotides are spatially separated from the nucleic acid molecule to be sequenced.
Figure 2:
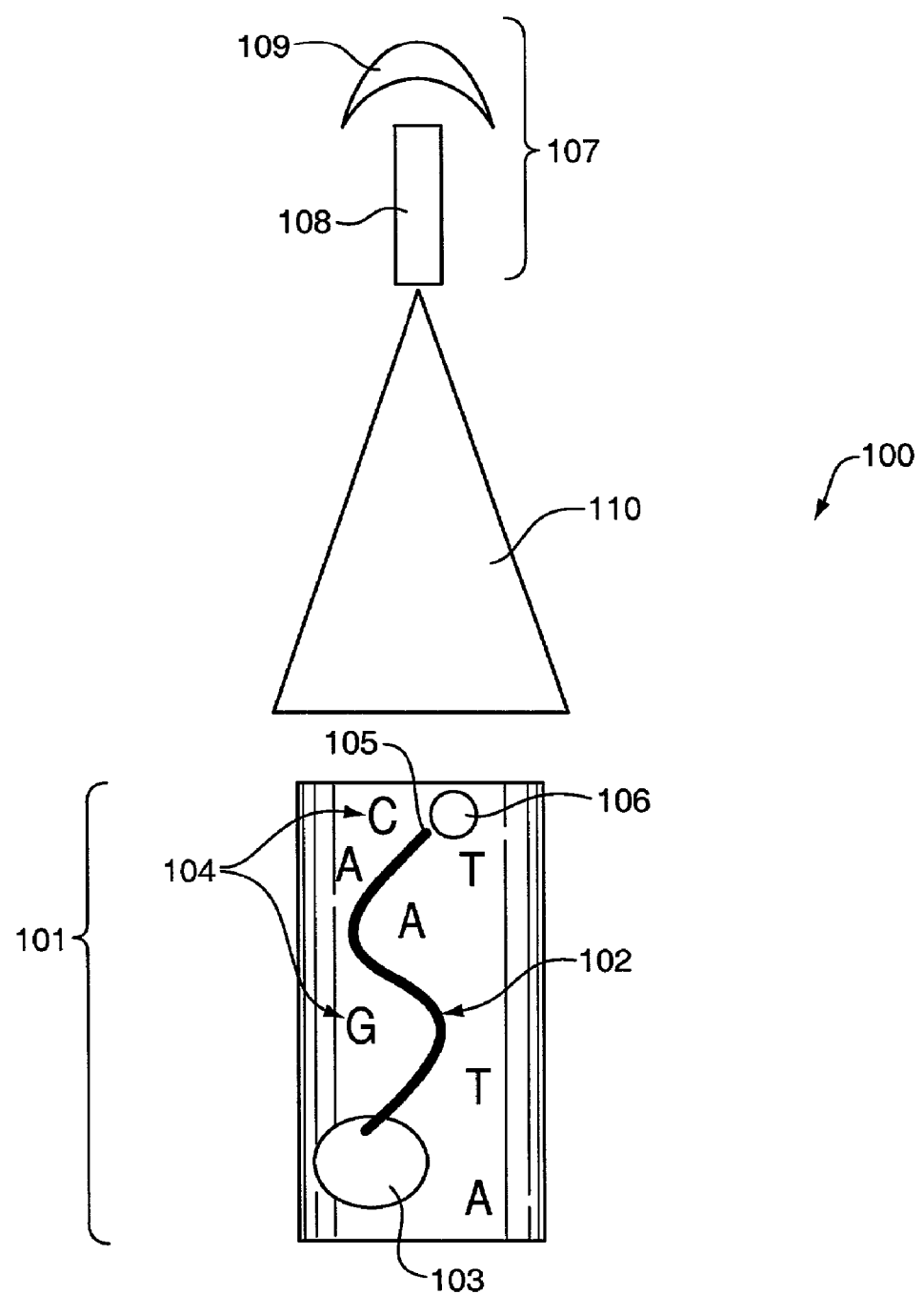
FIG. 2 illustrates an exemplary apparatus (not to scale) and method for DNA sequencing in which the released nucleotides are not spatially separated from the nucleic acid molecule. The detector quantifies the nucleotides present in solution.

In some embodiments, disclosed in FIG. 1 and FIG. 2, the methods involve sequencing of individual single-stranded nucleic acid molecules 13, 102 that are attached to an immobilization surface 14, 103 in a reaction chamber 11, 101 and disassembled in a deconstruction reaction. In such embodiments, the reaction chamber 11, 101 contains one or more deconstruction reagents 15, 106 that sequentially remove one nucleotide 16, 104 at a time from the unattached end 17, 105 of the nucleic acid molecule 13, 102. Non-limiting examples of such deconstruction reagents 15, 106 include any exonuclease known in the art. In some embodiments, the nucleotides 16, 104 are identified by Raman spectroscopy as they are released into solution.

Certain embodiments are illustrated in FIG. 1. FIG. 1 shows an apparatus 10 for nucleic acid sequencing comprising a reaction chamber 11 attached to a flow path 12. The reaction chamber 11 contains a nucleic acid molecule 13 attached to an immobilization surface 14 along with a deconstruction reagent 15, such as an exonuclease. The exonuclease 15 catalyzes the sequential release of individual nucleotides 16 from the free end 17 of the nucleic acid molecule 13. As the individual nucleotides 16 are released by the deconstruction reaction and enter solution, they move down the flow path 12 past a detection unit 18. The detection unit 18 comprises an excitation source 19, such as a laser, that emits an excitatory beam 20. The excitatory beam 20 interacts with the released nucleotides 16 so that electrons are excited to a higher energy state. The Raman emission spectrum that results from the return of the electrons to a lower energy state is detected by a Raman spectroscopic detector 21, such as a spectrometer or a monochromator.

In embodiments illustrated in FIG. 1, the released nucleotides 16 are spatially separated from the nucleic acid molecule 13 before detection by the detection unit 18. Spatial separation acts to increase the signal-to-noise ratio of the Raman detector 21 by isolating the individual nucleotides 16.

FIG. 1 illustrates embodiments in which a single nucleic acid molecule 13 is contained in a single reaction chamber 11. In alternative embodiments, multiple nucleic acid molecules 13, each in a separate reaction chamber 11, may be sequenced simultaneously. In such cases, the nucleic acid molecule 13 in each reaction chamber 11 may be identical or may be different. In other alternative embodiments, two or more nucleic acid molecules 13 may be present in a single reaction chamber 11. In such embodiments, the nucleic acid molecules 13 will be identical in sequence. Where more than one nucleic acid molecule 13 is present in the reaction chamber 11, the Raman emission signals will represent an average of the nucleotides 16 released simultaneously from all nucleic acid molecules 13 in the reaction chamber 11. The skilled artisan will be able to correct the signal obtained at any given time for deconstruction reactions that either lag behind or precede the majority of reactions occurring in the reaction chamber 11, using known data analysis techniques. In certain embodiments, the skilled artisan may use procedures to synchronize the deconstruction of multiple nucleic acid molecules 13 present in a single reaction chamber 11, as by adding a bolus of deconstruction reagents 15 with rapid mixing.

In certain alternative embodiments, a tag molecule may be added to the reaction chamber 11 or to the flow path 12 upstream of the detection unit 18. The tag molecule binds to and tags free nucleotides 16 as they are released from the nucleic acid molecule 13. This post-release tagging avoids problems that are encountered when the nucleotides 16 of the nucleic acid molecule 13 are tagged before their release into solution. For example, the use of bulky fluorescent probe molecules may provide considerable steric hindrance when each nucleotide 16 incorporated into a nucleic acid molecule 13 is labeled before deconstruction, reducing the efficiency and increasing the time required for the sequencing reaction.

In embodiments involving post-release tagging of nucleotides 16, it is contemplated that alternative methods of detection may be used, for example fluorescence spectroscopy or luminescence spectroscopy. Many alternative methods of detection of free nucleotides 16 in solution are known and may be used. For such methods, the Raman spectroscopic detection unit 18 may be replaced with a detection unit 18 designed to detect fluorescence, luminescence or other types of signals.

The tag molecules have unique and highly visible optical signatures that can be distinguished for each of the common nucleotides 16. In certain embodiments, the tag may serve to increase the strength of the Raman emission signal or to otherwise enhance the sensitivity or specificity of the Raman detector 21 for nucleotides 16. Non-limiting examples of tag molecules that could be used for embodiments involving Raman spectroscopy include TRIT (tetramethyl rhodamine isothiol), NBD (7-nitrobenz-2-oxa-1,3-diazole), Texas Red dye, phthalic acid, terephthalic acid, isophthalic acid, cresyl fast violet, cresyl blue violet, brilliant cresyl blue, para-aminobenzoic acid, erythrosine and aminoacridine. Other tag moieties that may be of use for particular embodiments include cyanide, thiol, chlorine, bromine, methyl, phosphorus and sulfur. In certain embodiments, carbon nanotubes may be of use as Raman tags. The use of tags in Raman spectroscopy is known in the art (e.g., U.S. Pat. Nos. 5,306,403 and 6,174,677). The skilled artisan will realize that Raman tags should generate distinguishable Raman spectra when bound to different nucleotides 16, or different labels should be designed to bind only one type of nucleotide 16.

In certain embodiments, the nucleic acid molecule 13 is fixed in place, as by attachment to an immobilization surface 14, and immersed in a microfluidic flow down a flow path 12 that transports the released nucleotides 16 away from the nucleic acid molecule 13 and past a detection unit 18. In non-limiting examples, the microfluidic flow may result from a bulk flow of solvent past the nucleic acid molecule 13 and down a flow path 12, for example, a microcapillary tube or an etched channel in a silicon, glass or other chip. In alternative embodiments, the bulk medium moves only slowly or not at all, but charged species within the solution (such as negatively charged nucleotides 16) move down a flow path 12 comprising a channel or tube in response to an externally applied electrical field.

In other alternative embodiments, the nucleic acid molecule 13 may be moved by moving the immobilization surface 14 to which it is attached away from the released nucleotides 16. The released nucleotides 16 may be scanned and identified by a moving detection unit 18 that follows the nucleic acid molecule 13.

In the embodiments discussed above, the detection unit 18 must be capable of distinguishing between the common nucleotides 16 released from the nucleic acid molecule 13. At a minimum, the detection unit 18 must be able to distinguish between nucleotides 16 containing adenosine (A), guanosine (G), cytosine (C) and thymidine (T) for sequencing DNA molecules 13. If RNA 13 is being sequenced, the detection unit 18 must be able to distinguish between nucleotides 16 containing A, G, C and uridine (U). With a single nucleic acid molecule 13 per reaction chamber 11, it is not necessary that the detection unit 18 be capable of quantifying the amounts of each nucleotide 16 in solution, since the nucleotides 16 move past the detection unit 18 one at a time.

In other embodiments, illustrated in FIG. 2, the detection unit 107 is sensitive enough to quantify the number of free nucleotides 104 present in solution. Thus, separation of released nucleotides 104 from the nucleic acid molecule 102 is not required. As illustrated in FIG. 2, the apparatus 100 comprises a reaction chamber 101 containing a nucleic acid molecule 102 attached at one end to an immobilization surface 103. Free nucleotides 104 are sequentially removed from the unattached end 105 of the nucleic acid molecule 102 by the action of a deconstruction reagent 106, such as an exonuclease.

As shown in FIG. 2, in these embodiments the free nucleotides 104 are not spatially segregated from the nucleic acid molecule 102. The detection unit 107, comprising an excitation source 108 emitting an excitation beam 110 and a detector 109, analyzes the reaction chamber 101 containing both nucleic acid molecule 102 and free nucleotides 104. Because the detector 109 can quantify the amount of each nucleotide 104 in solution, the nucleic acid 102 sequence can be determined by the temporal sequence of release of nucleotides 104 into solution. Because a greater volume is being scanned, it may be necessary to employ a more intense excitation beam 110 covering a broader area.

In these embodiments, as each successive nucleotide 104 is released from the unattached end 105 of the nucleic acid molecule 102, the nucleotide 104 is identified by the increase in signal for that nucleotide 104 in solution. The Raman detector 109 can separately quantify the number of molecules of each nucleotide 104—adenosine monophosphate (AMP), guanosine monophosphate (GMP), cytosine monophosphate (CMP) and uridine monophosphate (UMP) or thymidine monophosphate (TMP) in solution and separate those signals from the baseline Raman signals produced by the nucleic acid molecule 102.

The skilled artisan will realize that analysis of DNA 13, 102 will result in the release of deoxyribonucleosides or deoxyribonucleotides 16, 104 (including thymidine), while analysis of RNA 13, 102 will result in the release of ribonucleosides or ribonucleotides 16, 104 (including uridine). Although nucleoside monophosphates 16, 104 will generally be the form released by exonuclease 15, 106 activity, the embodiments are not limited to detection of any particular form of free nucleotide or nucleoside 16, 104 but encompass any monomer 16, 104 that may be released from a nucleic acid 13, 102 by the activity of a deconstruction reagent 15, 106.

In further embodiments, some combination of the methods and apparatus 10, 100 shown in FIG. 1 and FIG. 2 may be used. The method of FIG. 1 can use a less sensitive detector 21, but requires more complicated molecular transport procedures. The method of FIG. 2 has simplified molecular transport but requires a more sensitive detector 109. A variety of intermediate approaches may be used. For example, a microfluidics flow down a flow path 12 may be used to remove nucleotides 16 that have already been detected from the area illuminated by the excitation beam 20, while the quantification capability of the Raman detector 21 allows detection to occur in the absence of a specific temporal or spatial separation between the released nucleotides 16.

In certain embodiments, data from a detector 21, 109, such as a spectrometer or monochromator array, may flow to an information processing system that maintains a database associating specific Raman signatures with specific nucleotides 16, 104. The information processing system records the signatures detected by the detector 21, 109, correlates those signatures with the signatures of known nucleotides 16, 104 in the database, and maintains a record of nucleotide 16, 104 appearance that indicates the sequence of the nucleic acid molecule 13, 102. The information processing system may also perform standard procedures such as subtraction of background signals and "base-calling" determination when overlapping temporal or spatial signals are detected from more than one nucleotide 16, 104.

In certain embodiments, the nucleic acid molecule 13, 102 may be attached to a surface 14, 103 such as functionalized glass, silicon, PDMS (polydimethlyl siloxane), silver or other metal coated surfaces, quartz, plastic, PTFE (polytetrafluoroethylene), PVP (polyvinyl pyrrolidone), polystyrene, polypropylene, polyacrylamide, latex, nylon, nitrocellulose, a glass bead, a magnetic bead, or any other material known in the art that is capable of having functional groups such as amino, carboxyl, thiol, hydroxyl or Diels-Alder reactants incorporated on its surface 14, 103.

In some embodiments, functional groups may be covalently attached to cross-linking agents so that binding interactions between nucleic acid molecule 13, 102 and deconstruction reagent 15, 106 may occur without steric hindrance. Typical cross-linking groups include ethylene glycol oligomers and diamines. Attachment may be by either covalent or non-covalent binding. Various methods of attaching nucleic acid molecules 13, 102 to surfaces 14, 103 are known in the art and may be employed.

Definitions

As used herein, "a" or "an" may mean one or more than one of an item.

"Nucleic acid" 13, 102 encompasses DNA, RNA, single-stranded, double-stranded or triple stranded and any chemical modifications thereof, although single-stranded nucleic acids 13, 102 are preferred. Virtually any modification of the nucleic acid 13, 102 is contemplated. As used herein, a single stranded nucleic acid 13, 102 may be denoted by the prefix "ss", a double stranded nucleic acid 13, 102 by the prefix "ds", and a triple stranded nucleic acid 13, 102 by the prefix "ts."

A "nucleic acid" 13, 102 may be of almost any length, from 10, 20, 30, 40, 50, 60, 75, 100, 125, 150, 175, 200, 225, 250, 275, 300, 400, 500, 600, 700, 800, 900, 1000, 1500, 2000, 2500, 3000, 3500, 4000, 4500, 5000, 6000, 7000, 8000, 9000, 10,000, 15,000, 20,000, 30,000, 40,000, 50,000, 75,000, 100,000, 150,000, 200,000, 500,000, 1,000,000, 1,500,000, 2,000,000, 5,000,000 or even more bases in length, up to a full-length chromosomal DNA molecule 13, 102.

A "nucleoside" 16, 104 is a molecule comprising a base (A, C, G, T or U) covalently attached to a pentose sugar such as deoxyribose, ribose or derivatives or analogs of pentose sugars.

A "nucleotide" 16, 104 refers to a nucleoside further comprising at least one phosphate group covalently attached to the pentose sugar. In some embodiments, the nucleotides 16, 104 are ribonucleoside monophosphates 16, 104 or deoxyribonucleoside monophosphates 16, 104 although in certain embodiments it is anticipated that nucleoside diphosphates or triphosphates 16, 104 could be produced. In other embodiments, nucleosides 16, 104 may be released from the nucleic acid molecule 13, 102 and detected as discussed below. It is contemplated that various substitutions or modifications may be made in the structure of the nucleotides 16, 104, so long as they are still capable of being released from the nucleic acid 13, 102 by a deconstruction reagent 15, 106. For example, in certain embodiments the ribose or deoxyribose moiety may be substituted with another pentose sugar or a pentose sugar analog. In other embodiments, the phosphate groups may be substituted by various analogs.

Nucleic Acids

Nucleic acid molecules 13, 102 to be sequenced may be prepared by any technique known in the art. In certain embodiments, the nucleic acids 13, 102 are naturally occurring DNA or RNA molecules. Virtually any naturally occurring nucleic acid 13, 102 may be prepared and sequenced by the disclosed methods including, without limit, chromosomal, mitochondrial and chloroplast DNA and ribosomal, transfer, heterogeneous nuclear and messenger RNA.

Methods for preparing and isolating various forms of cellular nucleic acids 13, 102 are known. (See, e.g., *Guide to Molecular Cloning Techniques*, eds. Berger and Kimmel, Academic Press, New York, N.Y., 1987; *Molecular Cloning: A Laboratory Manual,* 2nd Ed., eds. Sambrook, Fritsch and Maniatis, Cold Spring Harbor Press, Cold Spring Harbor, N.Y., 1989). Generally, cells, tissues or other source material containing nucleic acids 13, 102 to be sequenced are first homogenized, for example by freezing in liquid nitrogen followed by grinding in a morter and pestle. Certain tissues may be homogenized using a Waring blender, Virtis homogenizer, Dounce homogenizer or other homogenizer. Crude homogenates may be extracted with detergents, such as sodium dodecyl sulphate (SDS), Triton X-100, CHAPS (3-[ (3-cholamidopropyl)-dimethylammonio]-1-propane sulfonate), octylglucoside or other detergents known in the art. Alternatively or in addition, extraction may use chaotrophic agents such as guanidinium isothiocyanate, or organic solvents such as phenol. In some embodiments, protease treatment, for example with proteinase K, may be used to degrade cell proteins. Particulate contaminants may be removed by centrifugation or ultracentrifugation (for example, 10 to 30 min at about 5,000 to 10,000×g, or 30 to 60 min at about 50,000 to 100,000×g). Dialysis against aqueous buffer of low ionic strength may be of use to remove salts or other soluble contaminants. Nucleic acids 13, 102 may be precipitated by addition of ethanol at −20° C., or by addition of sodium acetate (pH 6.5, about 0.3 M) and 0.8 volumes of 2-propanol. Precipitated nucleic acids 13, 102 may be collected by centrifugation or, for chromosomal DNA 13, 102, by spooling the precipitated DNA 13, 102 on a glass pipet or other probe.

The skilled artisan will realize that the procedures listed above are exemplary only and that many variations may be used, depending on the particular type of nucleic acid 13, 102 to be sequenced. For example, mitochondrial DNA 13, 102 is often prepared by cesium chloride density gradient centrifugation, using step gradients, while mRNA 13, 102 is often prepared using preparative columns from commercial sources, such as Promega (Madison, Wis.) or Clontech (Palo Alto, Calif.). Such variations are known in the art.

The skilled artisan will realize that depending on the type of nucleic acid 13, 102 to be prepared, various nuclease inhibitors may be used. For example, RNase contamination in bulk solutions may be eliminated by treatment with diethyl pyrocarbonate (DEPC). Commercially available nuclease inhibitors may be obtained from standard sources such as Promega (Madison, Wis.) or BRL (Gaithersburg, Md.). Purified nucleic acid 13, 102 may be dissolved in aqueous buffer, such as TE (Tris-EDTA) (ethylene diamine tetraacetic acid) and stored at −20° C. or in liquid nitrogen prior to use.

In cases where single stranded DNA (ssDNA) 13, 102 is to be sequenced, a ssDNA 13, 102 may be prepared from double stranded DNA (dsDNA) by standard methods. Most simply, dsDNA may be heated above its annealing temperature, at which point it spontaneously separates into ssDNA 13, 102. Representative conditions might involve heating at 92 to 95° C. for 5 min or longer. Formulas for determining conditions to separate dsDNA, based for example on GC content and the length of the molecule, are known in the art. Alternatively, single-stranded DNA 13, 102 may be prepared from double-stranded DNA by standard amplification techniques known in the art, using a primer that only binds to one strand of double-stranded DNA. Other methods of preparing single-stranded DNA 13, 102 are known in the art, for example by inserting the double-stranded nucleic acid to be sequenced into the replicative form of a phage like M13, and allowing the phage to produce single-stranded copies of the nucleic acid 13, 102.

Although certain embodiments concern preparation of naturally occurring nucleic acids 13, 102, virtually any type of nucleic acid 13, 102 that can serve as a substrate for an exonuclease or other deconstruction reagent 15, 106 could potentially be sequenced. For example, nucleic acids 13, 102 prepared by various amplification techniques, such as polymerase chain reaction (PCR™) amplification, could be sequenced. (See U.S. Pat. Nos. 4,683,195, 4,683,202 and 4,800,159.) Nucleic acids 13, 102 to be sequenced may alternatively be cloned in standard vectors, such as plasmids, cosmids, BACs (bacterial artificial chromosomes) or YACs (yeast artificial chromosomes). (See, e.g., Berger and Kimmel, 1987; Sambrook et al., 1989.) Nucleic acid inserts 13, 102 may be isolated from vector DNA, for example, by excision with appropriate restriction endonucleases, followed by agarose gel electrophoresis and ethidium bromide staining. Selected size-fractionated nucleic acids 13, 102 may be removed from gels, for example by the use of low melting point agarose or by electroelution from gel slices. Methods for isolation of insert nucleic acids 13, 102 are known in the art.

Isolation of Single Nucleic Acid Molecules

In certain embodiments, the nucleic acid molecule 13, 102 to be sequenced is a single molecule of ssDNA or ssRNA. A variety of methods for selection and manipulation of single ssDNA or ssRNA molecules 13, 102 may be used, for example, hydrodynamic focusing, micro-manipulator coupling, optical trapping, or a combination of these and similar methods. (See, e.g., Goodwin et al., 1996, Acc. Chem. Res. 29:607–619; U.S. Pat. Nos. 4,962,037; 5,405,747; 5,776, 674; 6,136,543; 6,225,068.)

In certain embodiments, microfluidics or nanofluidics may be used to sort and isolate nucleic acid molecules 13, 102. Hydrodynamics may be used to manipulate the movement of nucleic acids 13, 102 into a microchannel, microcapillary, or a micropore. In one embodiment, hydrodynamic forces may be used to move nucleic acid molecules 13, 102 across a comb structure to separate single nucleic acid molecules 13, 102. Once the nucleic acid molecules 13, 102 have been separated, hydrodynamic focusing may be used to position the molecules 13, 102 within the reaction chamber 11, 101. A thermal or electric potential, pressure or vacuum can also be used to provide a motive force for manipulation of nucleic acids 13, 102. In exemplary embodiments, manipulation of nucleic acids 13, 102 for sequencing may involve the use of a channel block design incorporating microfabricated channels and an integrated gel material, as disclosed in U.S. Pat. Nos. 5,867,266 and 6,214,246.

In another embodiment, a sample containing the nucleic acid molecule 13, 102 may be diluted prior to coupling to an immobilization surface 14, 103. In exemplary embodiments, the immobilization surface 14, 103 may be in the form of magnetic or nonmagnetic beads or other discrete structural units. At an appropriate dilution, each bead 14, 103 will have a statistical probability of binding zero or one nucleic acid molecule 13, 102. Beads 14, 103 with one attached nucleic acid molecule 13, 102 may be identified using, for example, fluorescent dyes and flow cytometer sorting or magnetic sorting. Depending on the relative sizes and uniformity of the beads 14, 103 and the nucleic acids 13, 102, it may be possible to use a magnetic filter and mass separation to separate beads 14, 103 containing a single bound nucleic acid molecule 13, 102. In other embodiments, multiple nucleic acids 13, 102 attached to a single bead or other immobilization surface 14, 103 may be sequenced.

In alternative embodiments, a coated fiber tip 14, 103 may be used to generate single molecule nucleic acids 13, 102 for sequencing (e.g., U.S. Pat. No. 6,225,068). In other alternative embodiments, the immobilization surfaces 14, 103 may be prepared to contain a single molecule of avidin or other cross-linking agent. Such a surface 14, 103 could attach a single biotinylated nucleic acid molecule 13, 102 to be sequenced. This embodiment is not limited to the avidin-biotin binding system, but may be adapted to any coupling system known in the art.

In other alternative embodiments, an optical trap may be used for manipulation of single molecule nucleic acid molecules 13, 102 for sequencing. (E.g., U.S. Pat. No. 5,776, 674). Exemplary optical trapping systems are commercially available from Cell Robotics, Inc. (Albuquerque, N. Mex.), S+L GmbH (Heidelberg, Germany) and P.A.L.M. Gmbh (Wolfratshausen, Germany).

Methods of Immobilization

In various embodiments, the nucleic acid molecules 13, 102 to be sequenced may be attached to a solid surface 14, 103 (or immobilized). Immobilization of nucleic acid molecules 13, 102 may be achieved by a variety of methods involving either non-covalent or covalent attachment between the nucleic acid molecule 13, 102 and the surface 14, 103. In an exemplary embodiment, immobilization may be achieved by coating a surface 14, 103 with streptavidin or avidin and the subsequent attachment of a biotinylated nucleic acid 13, 102 (Holmstrom et al., Anal. Biochem. 209:278–283, 1993). Immobilization may also occur by coating a silicon, glass or other surface 14, 103 with poly-L-Lys (lysine) or poly L-Lys, Phe (phenylalanine), followed by covalent attachment of either amino- or sulfhydryl-modified nucleic acids 13, 102 using bifunctional crosslinking reagents (Running et al., BioTechniques 8:276–277, 1990; Newton et al., Nucleic Acids Res. 21:1155–62, 1993). Amine residues may be introduced onto a surface 14, 103 through the use of aminosilane for cross-linking.

Immobilization may take place by direct covalent attachment of 5'-phosphorylated nucleic acids 13, 102 to chemically modified surfaces 14, 103 (Rasmussen et al., Anal. Biochem. 198:138–142, 1991). The covalent bond between the nucleic acid 13, 102 and the surface 14, 103 is formed by condensation with a water-soluble carbodiimide. This method facilitates a predominantly 5'-attachment of the nucleic acids 13, 102 via their 5'-phosphates.

DNA 13, 102 is commonly bound to glass by first silanizing the glass surface 14, 103, then activating with carbodiimide or glutaraldehyde. Alternative procedures may use reagents such as 3-glycidoxypropyltrimethoxysilane (GOP) or aminopropyltrimethoxysilane (APTS) with DNA 13, 102 linked via amino linkers incorporated either at the 3' or 5' end of the molecule. DNA 13, 102 may be bound directly to membrane surfaces 14, 103 using ultraviolet radiation. Other non-limiting examples of immobilization techniques for nucleic acids 13, 102 are disclosed in U.S. Pat. Nos. 5,610,287, 5,776,674 and 6,225,068.

The type of surface 14, 103 to be used for immobilization of the nucleic acid 13, 102 is not limiting. In various embodiments, the immobilization surface 14, 103 may be magnetic beads, non-magnetic beads, a planar surface, a pointed surface, or any other conformation of solid surface 14, 103 comprising almost any material, so long as the material is sufficiently durable and inert to allow the nucleic acid 13, 102 sequencing reaction to occur. Non-limiting examples of surfaces 14, 103 that may be used include glass, silica, silicate, PDMS, silver or other metal coated surfaces, nitrocellulose, nylon, activated quartz, activated glass, polyvinylidene difluoride (PVDF), polystyrene, polyacrylamide, other polymers such as poly(vinyl chloride), poly(methyl methacrylate) or poly(dimethyl siloxane), and photopolymers which contain photoreactive species such as nitrenes, carbenes and ketyl radicals capable of forming covalent links with nucleic acid molecules 13, 102 (See U.S. Pat. Nos. 5,405,766 and 5,986,076).

Bifunctional cross-linking reagents may be of use in various embodiments, such as attaching a nucleic acid molecule 13, 102 to a surface 14, 103. The bifunctional cross-linking reagents can be divided according to the specificity of their functional groups, e.g., amino, guanidino, indole, or carboxyl specific groups. Of these, reagents directed to free amino groups are popular because of their commercial availability, ease of synthesis and the mild reaction conditions under which they can be applied. Exemplary methods for cross-linking molecules are disclosed in U.S. Pat. Nos. 5,603,872 and 5,401,511. Cross-linking reagents include glutaraldehyde (GAD), bifunctional oxirane (OXR), ethylene glycol diglycidyl ether (EGDE), and carbodiimides, such as 1-ethyl-3-(3-dimethylaminopropyl) carbodiimide (EDC).

Deconstruction Reagent

The sequencing reaction involves binding of a deconstruction reagent 15, 106 to the free end 17, 105 of the nucleic acid molecule 13, 102 and removal of nucleotides 16, 104 one at a time. In certain embodiments the reaction may be catalyzed by an enzyme, such as an exonuclease 15, 106. The embodiments are not limited by the type of exonuclease 15, 106 that may be used. Non-limiting examples of exonucleases 15, 106 of potential use include E. coli exonuclease I, III, V or VII, Bal 31 exonuclease, mung bean exonuclease, S1 nuclease, E. coli DNA polymerase I holoenzyme or Klenow fragment, RecJ, exonuclease T, T4 or T7 DNA polymerase, iTaq polymerase, exonuclease T7 gene 6, snake venom phosphodiesterase, spleen phosphodiesterase, Thermococcus litoralis DNA polymerase, Pyrococcus sp. GB-D DNA polymerase, lambda exonuclease, S. aureus micrococcal nuclease, DNase I, ribonuclease A, T1 micrococcal nuclease, or other exonucleases known in the art. Exonucleases 15, 106 are available from commercial sources such as New England Biolabs (Beverly, Mass.), Amersham Pharmacia Biotech (Piscataway, N.J.), Promega (Madison, Wis.), Sigma Chemicals (St. Louis, Mo.) or Boehringer Mannheim (Indianapolis, Ind.).

The skilled artisan will realize that enzymes with exonuclease 15, 106 activity have various properties, for example, they can remove nucleotides 16, 104 from the 5' end, the 3' end, or either end of the nucleic acid molecule 13, 102. They can show specificity for RNA, DNA or both RNA and DNA 13, 102. Their activity may depend on the use of either single or double-stranded nucleic acids 13, 102. They may be differentially affected by various characteristics of the reaction medium, such as salt, temperature, pH, or divalent cations. These and other properties of the various exonucleases and polymerases 15, 106 are known in the art.

The skilled artisan will realize that the rate of exonuclease 15, 106 activity may be manipulated to coincide with the optimal rate of analysis of nucleotides 16, 104 by the detection unit 18, 107. Various methods are known for adjusting the rate of exonuclease 15, 106 activity, including adjusting the temperature, pressure, pH, salt concentration or divalent cation concentration in the reaction chamber 11, 101. Methods of optimization of exonuclease 15, 106 activity are known in the art.

Labels

Certain embodiments may involve incorporating a label into the nucleotides 16, 104, to facilitate their measurement by the detection unit 18, 107. A number of different labels may be used, such as Raman tags, fluorophores, chromophores, radioisotopes, enzymatic tags, antibodies, chemiluminescent, electroluminescent, affinity labels, etc. One of skill in the art will recognize that these and other label moieties not mentioned herein can be used in various embodiments.

Labels for use in embodiments involving Raman spectroscopy are discussed above. In other embodiments, the label moiety to be used may be a fluorophore, such as Alexa 350, Alexa 430, AMCA (7-amino-4-methylcoumarin-3-acetic acid), BODIPY (5,7-dimethyl-4-bora-3a,4a-diaza-s-indacene-3-propionic acid) 630/650, BODIPY 650/665, BODIPY-FL (fluorescein), BODIPY-R6G (6-carboxyrhodamine), BODIPY-TMR (tetramethylrhodamine), BODIPY-TRX (Texas Red-X), Cascade Blue, Cy2 (cyanine), Cy3, Cy5,6-FAM (5-carboxyfluorescein), Fluorescein, 6-JOE (2'7'-dimethoxy-4'5'-dichloro-6-carboxyfluorescein), Oregon Green 488, Oregon Green 500, Oregon Green 514, Pacific Blue, Rhodamine Green, Rhodamine Red, ROX (6-carboxy-X-rhodamine), TAMRA (N,N,N',N'-tetramethyl-6-carboxyrhodamine), Tetramethylrhodamine, and Texas Red. Fluorescent or luminescent labels can be obtained from standard commercial sources, such as Molecular Probes (Eugene, Oreg.).

Reaction Chamber

The reaction chamber 11, 101 is designed to hold the immobilization surface 14, 103, nucleic acid molecule 13, 102, deconstruction reagent 15, 106 and nucleotides 16, 104 in an aqueous environment. In some embodiments, the reaction chamber 11, 101 is designed to be temperature controlled, for example by incorporation of Pelletier elements or other methods known in the art. Methods of controlling temperature for low volume liquids are known in the art. (See, e.g., U.S. Pat. Nos. 5,038,853, 5,919,622, 6,054,263 and 6,180,372.)

In certain embodiments, the reaction chamber 11, 101 and any associated fluid channels, for example, the flow path 12 or channels to provide connections to a waste port, to a nucleic acid 13, 102 loading port, or to a source of deconstruction reagent 15, 106 are manufactured in a batch fabrication process, as known in the fields of computer chip manufacture or microcapillary chip manufacture. In some embodiments, the reaction chamber 11, 101 and other components of the apparatus 10, 100, such as the flow path 12, may be manufactured as a single integrated chip. Such a chip may be manufactured by methods known in the art, such as by photolithography and etching. However, the manufacturing method is not limiting and other methods known in the art may be used, such as laser ablation, injection molding, casting, or imprinting techniques. Methods for manufacture of nanoelectromechanical systems may be used for certain embodiments. (See, e.g., Craighead, Science 290:1532–36, 2000.) Microfabricated chips are commercially available from sources such as Caliper Technologies Inc. (Mountain View, Calif.) and ACLARA BioSciences Inc. (Mountain View, Calif.).

In a non-limiting example, Borofloat glass wafers (Precision Glass & Optics, Santa Ana, Calif.) may be pre-etched for a short period in concentrated HF (hydrofluoric acid) and cleaned before deposition of an amorphous silicon sacrificial layer in a plasma-enhanced chemical vapor deposition (PECVD) system (PEII-A, Technics West, San Jose, Calif.). Wafers may be primed with hexamethyldisilazane (HMDS), spin-coated with photoresist (Shipley 1818, Marlborough, Mass.) and soft-baked. A contact mask aligner (Quintel Corp. San Jose, Calif.) may be used to expose the photoresist layer with one or more mask designs, and the exposed photoresist removed using a mixture of Microposit developer concentrate (Shipley) and water. Developed wafers may be hard-baked and the exposed amorphous silicon removed using $CF_4$ (carbon tetrafluoride) plasma in a PECVD reactor. Wafers may be chemically etched with concentrated HF to produce the reaction chamber 11, 101, flow path 12 and any channels. The remaining photoresist may be stripped and the amorphous silicon removed.

Access holes may be drilled into the etched wafers with a diamond drill bit (Crystalite, Westerville, Ohio). A finished chip may be prepared by thermally bonding an etched and drilled plate to a flat wafer of the same size in a programmable vacuum furnace (Centurion VPM, J. M. Ney, Yucaipa, Calif.). In certain embodiments, the chip may be prepared by bonding two etched plates to each other. Alternative exemplary methods for fabrication of a chip incorporating a reaction chamber 11, 101 and flow path 12 are disclosed in U.S. Pat. Nos. 5,867,266 and 6,214,246.

To facilitate detection of nucleotides 16, 104 by the detection unit 18, 107 the material comprising the reaction chamber 11, 101 and/or flow path 12 may be selected to be transparent to electromagnetic radiation at the excitation and emission frequencies used for the detection unit 18, 107. Glass, silicon, and any other materials that are generally transparent in the frequency ranges used for Raman spectroscopy, fluorescence spectroscopy, luminescence spectroscopy, or other forms of spectroscopy may be used. In some embodiments the surfaces of the reaction chamber 11, 101 and/or flow path 12 that are opposite the detection unit 18, 107 may be coated with silver, gold, platinum, copper, aluminum or other materials that are relatively opaque to the detection unit 18, 107. In that position, the opaque material is available to enhance the Raman or other signal, for example by surface enhanced Raman spectroscopy, while not interfering with the function of the detection unit 18, 107. Alternatively, the reaction chamber 11, 101 and/or flow path 12 may contain a mesh comprising silver, gold, platinum, copper or aluminum. The skilled artisan will realize that in embodiments involving a flow path 12, the nucleotides 16 will generally be detected while they are in the flow path 12. In embodiments without a flow path 12, the nucleotides 104 will be detected in the reaction chamber 101.

In various embodiments, the reaction chamber 11, 101 may have an internal volume of about 1 picoliter, about 2 picoliters, about 5 picoliters, about 10 picoliters, about 20 picoliters, about 50 picoliters, about 100 picoliters, about 250 picoliters, about 500 picoliters, about 1 nanoliter, about 2 nanoliters, 5 nanoliters, about 10 nanoliters, about 20 nanoliters, about 50 nanoliters, about 100 nanoliters, about 250 nanoliters, about 500 nanoliters, about 1 microliter, about 2 microliters, about 5 microliters, about 10 microliters, about 20 microliters, about 50 microliters, about 100 microliters, about 250 microliters, about 500 microliters, or about 1 milliliter.

Flow Path

In certain embodiments, the free nucleotides 16 are moved down a flow path 12 past the detection unit 18. A non-limiting example of techniques for transport of free nucleotides 16 includes microfluidic techniques. The flow path 12 can comprise a microcapillary (available, e.g., from ACLARA BioSciences Inc., Mountain View, Calif.) or a liquid integrated circuit (e.g., Caliper Technologies Inc., Mountain View, Calif.). Such microfluidic platforms require only nanoliter volumes of sample.

In certain embodiments, the free nucleotides 16 to be detected move down the flow path 12 by bulk flow of solvent. In other embodiments, microcapillary electrophoresis may be used to transport free nucleotides 16 down the flow path 12 and past the detection unit 18. Microcapillary electrophoresis generally involves the use of a thin capillary or channel that may or may not be filled with a particular separation medium. Electrophoresis of appropriately charged molecular species, such as negatively charged nucleotides 16, occurs in response to an imposed electrical field, negative on the reaction chamber 11 side of the apparatus and positive on the detection unit 18 side. Although electrophoresis is often used for size separation of a mixture of components that are simultaneously added to the microcapillary, it can also be used to transport similarly sized nucleotides 16 that are sequentially added to the flow path 12. Because the purine nucleotides (A, G) 16 are larger than the pyrimidine nucleotides (C, T, U) 16 and would therefore migrate more slowly, the length of the flow path 12 and corresponding transit time past the detector unit 18 should be kept to a minimum to prevent differential migration from mixing up the order of nucleotides 16 released from the nucleic acid 13. Alternatively, the separation medium filling the microcapillary may be selected so that the migration rates of purine and pyrimidine nucleotides 16 down the flow path 12 are similar or identical. Methods of microcapillary electrophoresis have been disclosed, for example, by Woolley and Mathies (*Proc. Natl. Acad. Sci. USA* 91:11348–352, 1994).

Microfabrication of microfluidic devices, including microcapillary electrophoretic devices has been discussed in, e.g., Jacobsen et al. (*Anal. Biochem,* 209:278–283,1994); Effenhauser et al. (*Anal. Chem.* 66:2949–2953, 1994); Harrison et al. (*Science* 261:895–897, 1993) and U.S. Pat. No. 5,904,824. Typically, these methods comprise photolithographic etching of micron scale channels on silica, silicon or other crystalline substrates or chips, and can be readily adapted for use. In some embodiments, the microcapillary may be fabricated from the same polymeric materials described for the fabrication of the reaction chamber 11, 101, using injection molding or other techniques known in the art.

Detection Unit

Embodiments Involving Raman Spectroscopy

In some embodiments, the detection unit 18, 107 is designed to detect and quantify nucleotides 16, 104 by Raman spectroscopy. Various methods for detection of nucleotides 16, 104 by Raman spectroscopy are known in the art. (See, e.g., U.S. Pat. Nos. 5,306,403; 6,002,471; 6,174,677). Variations on surface enhanced Raman spectroscopy (SERS) or surface enhanced resonance Raman spectroscopy (SERRS) have been disclosed. In SERS and SERRS, the sensitivity of the Raman detection is enhanced by a factor of $10^6$ or more for molecules adsorbed on roughened metal surfaces, such as silver, gold, platinum, copper or aluminum surfaces.

A non-limiting example of a Raman detection unit 18, 107 is disclosed in U.S. Pat. No. 6,002,471. In this embodiment, the excitation beam 20, 110 is generated by either a Nd:YAG laser 19, 108 at 532 nm wavelength or a Ti:sapphire laser 19, 108 at 365 nm wavelength. Pulsed laser beams 20, 110 or continuous laser beams 20, 110 may be used. The excitation beam 20, 110 passes through confocal optics and a microscope objective, and is focused onto the flow path 12 or the reaction chamber 101. The Raman emission light from the nucleotides 16, 104 is collected by the microscope objective and the confocal optics and is coupled to a monochromator for spectral dissociation. The confocal optics includes a combination of dichroic filters, barrier filters, confocal pinholes, lenses, and mirrors for reducing the background signal. Standard full field optics can be used as well as confocal optics. The Raman emission signal is detected by a Raman detector 21, 109. The detector 21, 109 includes an avalanche photodiode interfaced with a computer for counting and digitization of the signal. In certain embodiments, a mesh comprising silver, gold, platinum, copper or aluminum may be included in the flow path 12 or the reaction chamber 101 to provide an increased signal due to surface enhanced Raman or surface enhanced Raman resonance.

Alternative embodiments of detection units 18, 107 are disclosed, for example, in U.S. Pat. No. 5,306,403, including a Spex Model 1403 double-grating spectrophotometer 21, 109 equipped with a gallium-arsenide photomultiplier tube (RCA Model C31034 or Burle Industries Model C3103402) operated in the single-photon counting mode. The excitation source 19, 108 is a 514.5 nm line argon-ion laser 19, 108 from SpectraPhysics, Model 166, and a 647.1 nm line of a krypton-ion laser 19, 108 (Innova 70, Coherent).

Alternative excitation sources 19, 108 include a nitrogen laser 19, 108 (Laser Science Inc.) at 337 nm and a helium-cadmium laser 19, 108 (Liconox) at 325 nm (U.S. Pat. No. 6,174,677). The excitation beam 20, 110 may be spectrally purified with a bandpass filter (Corion) and may be focused on the flow path 12 or reaction chamber 101 using a 6× objective lens (Newport, Model L6X). The objective lens may be used to both excite the nucleotides 16, 104 and to collect the Raman signal, by using a holographic beam splitter (Kaiser Optical Systems, Inc., Model HB 647-26N18) to produce a right-angle geometry for the excitation beam 20, 110 and the emitted Raman signal. A holographic notch filter (Kaiser Optical Systems, Inc.) may be used to reduce Rayleigh scattered radiation. Alternative Raman detectors 21, 109 include an ISA HR-320 spectrograph equipped with a red-enhanced intensified charge-coupled device (RE-ICCD) detection system (Princeton Instruments). Other types of detectors 21, 109 may be used, such as charged injection devices, photodiode arrays or phototransistor arrays.

Any suitable form or configuration of Raman spectroscopy or related techniques known in the art may be used for detection of nucleotides 16, 104, including but not limited to normal Raman scattering, resonance Raman scattering, surface enhanced Raman scattering, surface enhanced resonance Raman scattering, coherent anti-Stokes Raman spectroscopy (CARS), stimulated Raman scattering, inverse Raman spectroscopy, stimulated gain Raman spectroscopy, hyper-Raman scattering, molecular optical laser examiner (MOLE) or Raman microprobe or Raman microscopy or confocal Raman microspectrometry, three-dimensional or scanning Raman, Raman saturation spectroscopy, time resolved resonance Raman, Raman decoupling spectroscopy or UV-Raman microscopy.

Embodiments Involving FRET

In certain alternative embodiments, the nucleotides 16, 104 are identified and quantified using fluorescence resonance energy transfer (FRET). FRET is a spectroscopic phenomenon used to detect proximity between a donor molecule and an acceptor molecule. The donor and acceptor pairs are chosen such that fluorescent emission from the donor overlaps the excitation spectrum of the acceptor. When the two molecules are associated (at a distance of less than 100 Angstroms), the excited-state energy of the donor is transferred non-radiatively to the acceptor and the donor emission is quenched. If the acceptor molecule is a fluorophore then its emission is enhanced. Compositions and methods for use of FRET with oligonucleotides are known in the art (e.g., U.S. Pat. No. 5,866,366).

Molecules that are frequently used as tags for FRET include fluorescein, 5-carboxyfluorescein (FAM), 2'7'- dimethoxy-4'5'-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), and 5-(2'-aminoethyl)aminonaphthalene-1-sulfonic acid (EDANS). Other potential FRET donor or acceptor molecules are known in the art (See U.S. Pat. No. 5,866,336, Table 1). The skilled artisan will be familiar with the selection of pairs of tag molecules for FRET (U.S. Pat. No. 5,866,336).

In embodiments involving FRET, the donor and acceptor molecules may be covalently or non-covalently attached to various constituents of the sequencing apparatus 10, 100. In certain embodiments, the donor or acceptor molecules may be attached to the nucleotides 16, 104, to the exonuclease 15, 106, or to the flow path 12.

In certain embodiments, the donor molecule may be attached to the exonuclease 15, 106 or to the surface of the flow path 12 and the acceptor molecules attached to the nucleotides 16, 104. In this case, each type of nucleotide 16, 104 should be attached to an acceptor molecule with a distinguishable emission spectrum, while the donor molecule should be selected to have a broad emission spectrum that overlaps with the excitation spectra for all four of the acceptor molecules. Multiple donor molecules may be present on the exonuclease 15, 106 or flow path 12, although in other embodiments only a single donor molecule may be present Upon excitation, the donor molecules will transfer their energy to the acceptor tag molecules attached to the nucleotides 16, 104, resulting in an enhanced emission signal from the acceptor molecules. Because the strength of the signal enhancement decreases rapidly with distance, the greatest signal enhancement will occur for nucleotides 16, 104 that are very close to the donor molecule(s). In the case of a donor molecule attached to the exonuclease 15, 106, at or near the catalytic site, the nucleotide 16, 104 with the strongest emission signal will be located at the catalytic site of the exonuclease 15, 106. The donor molecule should be attached close to the catalytic site, but in a position where it will not interfere with the exonuclease activity of the deconstruction reagent 15, 106. In embodiments where donor molecules are attached to the surface of the flow path 12 in the location where the excitation beam 20 is focused, only nucleotides 16 within the focus of the excitation beam 20 should give a detectable fluorescent signal. The wavelength of the excitation beam 20, 110 may be selected to maximally excite the donor molecules, while only weakly exciting the acceptor molecules. As each nucleotide 16, 104 is removed from the nucleic acid molecule 13, 102, the signal from its donor tag will be detected.

In certain embodiments, the template nucleic acid 13, 102 to be sequenced may be held within the field of view of a fluorescence microscope by methods known in the art, for example by use of an optical trap (e.g., U.S. Pat. No. 6,136,543). A non-limiting example of a fluorescence microscope that may be used is an inverted phase-contrast and incident-light fluorescence microscope (IMT2-RFC, Olympus Co., Ltd.), using an oil-immersed 100 power lens (Plan. multidot. Apochromat. times. 100, 1.40 NA, Olympus Co., Ltd.) The excitation beam 20, 110 may be emitted by a laser 19, 108, as discussed above. Fluorescence emission may be collected through the objective lens, using appropriate filters, and detected using any sensitive fluorescence detector 21, 109, such as a CCD device, photodiodes, photomultiplier tubes, or the equivalent.

Information Processing and Control System and Data Analysis

In certain embodiments, the nucleic acid sequencing apparatus 10, 100 may comprise an information processing system. The embodiments are not limiting for the type of information processing system used. An exemplary information processing system may incorporate a computer comprising a bus for communicating information and a processor for processing information. In one embodiment, the processor is selected from the Pentium® family of processors, including without limitation the Pentium® II family, the Pentium® III family and the Pentium® 4 family of processors available from Intel Corp. (Santa Clara, Calif.). In alternative embodiments, the processor may be a Celeron®, an Itanium®, or a Pentium Xeon® processor (Intel Corp., Santa Clara, Calif.). In various other embodiments, the processor may be based on Intel® architecture, such as Intel® IA-32 or Intel® IA-64 architecture. Alternatively, other processors may be used.

The computer may further comprise a random access memory (RAM) or other dynamic storage device, a read only memory (ROM) or other static storage and a data storage device such as a magnetic disk or optical disc and its corresponding drive. The information processing system may also comprise other peripheral devices known in the art, such a display device (e.g., cathode ray tube or Liquid Crystal Display), an alphanumeric input device (e.g., keyboard), a cursor control device (e.g., mouse, trackball, or cursor direction keys) and a communication device (e.g., modem, network interface card, or interface device used for coupling to Ethernet, token ring, or other types of networks).

In particular embodiments, the detection unit 18, 107 may be operably coupled to the information processing system. Data from the detection unit 18, 107 may be processed by the processor and data stored in the main memory. Data on emission profiles for standard nucleotides 16, 104 may also be stored in main memory or in ROM. The processor may compare the emission spectra from nucleotides 16, 104 in the reaction chamber 101 or the flow path 12 to identify the type of nucleotide 16, 104 released from the nucleic acid molecule 13, 102. The main memory may also store the sequence of nucleotides 16, 104 released from the nucleic acid molecule 13, 102. The processor may analyze the data from the detection unit 18, 107 to determine the sequence of the nucleic acid 13, 102. It is appreciated that a differently equipped information processing system may be used for certain implementations. Therefore, the configuration of the system may vary in different embodiments.

It should be noted that, while the processes described herein may be performed under the control of a programmed processor, in alternative embodiments, the processes may be fully or partially implemented by any programmable or hardcoded logic, such as Field Programmable Gate Arrays (FPGAs), TTL logic, or Application Specific Integrated Circuits (ASICs), for example. Additionally, the disclosed methods may be performed by any combination of programmed general purpose computer components and/or custom hardware components.

Following the data gathering operation, the data will typically be reported to a data analysis operation. To facilitate the analysis operation, the data obtained by the detection unit 18, 109 will typically be analyzed using a digital computer such as that described above. Typically, the computer will be appropriately programmed for receipt and storage of the data from the detection unit 18, 109 as well as for analysis and reporting of the data gathered.

In certain embodiments, custom designed software packages may be used to analyze the data obtained from the detection unit 18, 109. In alternative embodiments, data analysis may be performed, using an information processing system and publicly available software packages. Non-limiting examples of available software for DNA sequence analysis include the PRISM™ DNA Sequencing Analysis Software (Applied Biosystems, Foster City, Calif.), the Sequencher™ package (Gene Codes, Ann Arbor, Mich.), and a variety of software packages available through the National Biotechnology Information Facility at website www.nbif.org/links/1.4.1.php.

What is claimed is:

1. An apparatus comprising:
   a) a reaction chamber to contain an immobilization surface, the immobilization surface to attach one or more unlabeled nucleic acid molecules;
   b) a flow path attached to the reaction chamber;
   c) a liquid in the flow path;
   d) one or more unlabeled nucleotides free in solution in the liquid at the point of nucleotide detection; and
   e) a detection unit programmed to detect only the unlabeled nucleotides free in a liquid solution as they move past the detection unit, the detection unit comprising an excitation source and a Raman spectroscopic detector.

2. The apparatus of claim 1, wherein the excitation source is a laser.

3. The apparatus of claim 1, wherein the Raman detector is a spectrometer or monochromoator.

4. The apparatus of claim 1, further comprising (i) an information processing system; and (ii) a database.

5. The apparatus of claim 1, wherein the flow path comprises a microcapillary or one or more microchannels in a chip.

6. The apparatus of claim 1, wherein a portion of the flow path is coated with silver, gold, platinum, copper or aluminum.

7. The apparatus of claim 1, wherein the flow path contains a silver, gold, platinum, copper or aluminum mesh.

8. The apparatus of claim 1, further comprising an exonuclease.

9. An apparatus comprising:
   a) a reaction chamber to contain an immobilization surface, the immobilization surface to attach one or more unlabeled nucleic acid molecules;
   b) an exonuclease in the reaction chamber;
   c) at least a portion of the reaction chamber having a silver, gold, platinum, copper or aluminum mesh;
   d) one or more unlabeled nucleotides free in a liquid solution at the point of nucleotide detection; and
   e) a detection unit programmed to detect only the unlabeled nucleotides free in a liquid solution as they move past the detection unit, the detection unit comprising an excitation source and a Raman spectroscopic detector.

10. The apparatus of claim 1, wherein the nucleotides in solution are selected from the group consisting of adenosine monophosphate, guanosine monophosphate, cytosine monophosphate, uridine monophosphate and thymidine monophosphate.

11. The apparatus of claim 9, further comprising one or more nucleic acid molecules attached to an immobilization surface.

12. The apparatus of claim 1, wherein the nucleotides in solution move past the detection unit one nucleotide at a time.

13. The apparatus of claim 1, wherein the detection unit detects unlabeled nucleotides by unenhanced Raman spectroscopy, resonance Raman scattering, coherent anti-Stokes Raman spectroscopy (CARS), stimulated Raman scattering, inverse Raman spectroscopy, stimulated gain Raman spectroscopy, hyper-Raman scattering, molecular optical laser examiner (MOLE), Raman microprobe, Raman microscopy, confocal Raman microspectrometry, three-dimensional or scanning Raman spectroscopy, Raman saturation spectioscopy, time resolved resonance Raman spectroscopy, Raman decoupling spectroscopy, or UV-Raman microscopy.

14. The apparatus of claim 9, further comprising an exonuclease.

15. The apparatus of claim 1, wherein the detection unit comprises a mechanism to move the detection unit to follow the nucleotides as they move.

16. An apparatus comprising:
   a) a reaction chamber to contain an immobilization surface, the immobilization surface to attach one or more unlabeled nucleic acid molecules;
   b) a flow path attached to the reaction chamber, at least a portion of the flow path having a metal coating comprising silver, gold, platinum, copper or aluminum;
   c) a liquid in the flow path;
   d) one or more unlabeled nucleotides free in solution in the liquid at the point of nucleotide detection; and
   e) a detection unit programmed to detect only the unlabeled nucleotides free in a liquid solution as they move past the detection unit, the detection unit comprising an excitation source and a Raman spectroscopic detector.

* * * * *